United States Patent [19]

Suzuki et al.

[11] Patent Number: 4,941,346

[45] Date of Patent: Jul. 17, 1990

[54] VIBRATION-TYPE RHEOMETER APPARATUS

[75] Inventors: Osamu Suzuki; Syousuke Ishiwata; Mitsuroh Hayashi; Hideaki Oshima, all of Saitama, Japan

[73] Assignee: Chichibu Cement Kabushiki Kaisha, Japan

[21] Appl. No.: 273,273

[22] Filed: Nov. 18, 1988

[30] Foreign Application Priority Data

Nov. 18, 1987 [JP] Japan .................. 62-289521

[51] Int. Cl.⁵ ........................................... G01N 11/10
[52] U.S. Cl. .......................................... 73/54
[58] Field of Search .................... 73/59, 54

[56] References Cited

U.S. PATENT DOCUMENTS

| 4,166,381 | 9/1979 | Woo | 73/54 |
| 4,602,505 | 7/1986 | Kanda et al. | 73/54 |
| 4,729,237 | 3/1988 | Suzuki et al. | 73/54 |

FOREIGN PATENT DOCUMENTS

| 899057 | 3/1945 | France | 73/54 |
| 28400 | 3/1965 | Japan | 73/54 |
| 135337 | 8/1982 | Japan | 73/54 |
| 612160 | 6/1978 | U.S.S.R. | 73/54 |

Primary Examiner—Hezron E. Williams
Attorney, Agent, or Firm—Bruce L. Adams; Van C. Wilks

[57] ABSTRACT

A vibration-type rheometer comprises a vibration-type viscometer having a pair of vibrator subassemblies which resonate as in a tuning fork. The pair of vibrator subassemblies constituting a tuning fork vibrator each has at its free end a sensor plate formed from a thin metal plate places into a sample to be measured, and the vibrator subassemblies are driven at the same frequency but in opposite phase relationship to each other by an electromagnetic driving unit together with the sensor plates. A control unit supplies a time-varying driving current whose magnitude varies with time to the electromagnetic driving unit in order to change the vibration-applying force applied to the pair of vibrator subassemblies. The amplitude of vibration of the vibrator subassemblies changes as a function of the viscous resistance encountered by the sensor plates from the sample and the amplitude is electrically detected, and the detected value is sent to a recording unit together with the value of the driving current to thereby indicate the behavior of the sample.

17 Claims, 3 Drawing Sheets

VIBRATION-TYPE RHEOMETER APPARATUS

FIELD OF THE INVENTION

The present invention relates to a rheometer for measuring a phenomenon such as the deformation and flow of a fluid, and more particularly, to a vibration-type rheometer including a pair of tuning fork-like members capable of being vibrated in a fluid sample.

BACKGROUND OF THE INVENTION

A flowability of simple liquids, for example, such as water, alcohol, glycerine or the like, is different in viscosity, but these liquids exhibit a Newtonian viscosity, that is, a straining rate proportional to a stress during the flow. On the other hand, it has been known that thick liquids having a relatively complicated construction, for example, such as paint, toothpaste, mayonnaise and cold cream, exhibit a non-Newtonian viscosity which will not start the flow unless an external force exceeds a predermined value. On the other hand, the property of gels which change into sol when subjected to shaking or vibration, and then return again to gels when left standing is called thixotropy.

A measurement of Newtonian viscosity or non-Newtonian viscosity, particularly, the degree of thixotropy, can be determined by evaluating an area of a hysteresis loop based on the number of revolutions of a rotary viscometer. In the rotary viscometer, the viscosity is obtained by rotating a cylindrical body in a viscous fluid and measuring a torque due to the viscosity exerted on the cylindrical body. In a coaxial double cylindrical meter, a fluid is put between an inner tube and an outer tube, and a torque exerted on the inner tube when the outer tube is rotated is measured. This measurement is carried out by hanging the inner tube by means of a torsion wire and obtaining a torsional angle of the torsion wire. If a design is made so that an angular velocity of a rotary body is made variable so as to vary a shear rate corresponding thereto, it can be applied to the measurement of the flow characteristics of non-Newtonian viscous fluids.

However, it is necessary to vary the shape of a rotary body depending on a sample to be measured. Furthermore, since it is cumbersome to clean and wash the rotary body after being used, a problem arises in handling and using the apparatus. In addition, being affected by the inertia of the rotary body or by the flow of the sample, the range of a controllable angular velosity of the rotary body is narrow, and various measuring patterns cannot be selected.

SUMMARY OF THE INVENTION

It is a general object of the present invention to provide a new rheometer apparatus which can eliminate the disadvantages as noted above with respect to a rheometer using a conventional rotary viscometer.

Particularly, it is an object of the present invention to provide a rheometer which can widely change the manner of applying an external force to a sample to be measured and a strain rate so that various measuring patterns may be selected.

It is a further object of the present invention to provide a rheometer which is simple in handling and easy in operation.

According to the present invention, a vibration-type rheometer apparatus includes a viscometer having a pair of tuning fork-like members capable of being vibrated in a sample. A vibration-type viscometer having a pair of tuning fork-like members is known from U.S. Pat. No. 4,602,505 (corresponding to Europe Patent Laid-Open No. 112,156) entitled "APPARATUS FOR MEASURING VISCOSITY" issued to the present inventors on July 29, 1986. Also, an improved vibration-type viscometer of this type has been proposed in U.S. Pat. No. 4,729,237 (corresponding to Europe Patent Laid-Open No. 233,408) entitled "TUNING FORK VIBRATION-TYPE VISCOSITY MEASURING APPARATUS" issued to the present inventors on Mar. 8, 1988. These vibration-type viscometers each comprise a tuning fork vibrator including a pair of vibrator subassemblies, each vibrator subassembly having at its free end a sensor plate to be inserted into a sample to be measured, a driving unit for applying vibrations to the pair of vibrator subassemblies, and a detector for detecting the vibration amplitude of the pair of vibrator subassemblies which changes due to a viscosity resistance applied to the sensor plates when placed in the sample and for converting the vibration amplitude into an electric signal. The driving unit comprises a combination of an electromagnetic coil and a permanent magnet, in which the pair of vibrator subassemblies are vibrated in a phase opposite to each other, that is, a phase difference of 180 degrees under the same frequency. In the vibation-type viscometers so far proposed, the driving frequency is 30 Hz, and one-side amplitude at the time of no-load is 20 microns, which is constant.

A characteristic of the present invention resides in the further provision of a control unit for changing the driving current applied to the aforesaid driving unit according to a predetermined pattern, and a recording means for plotting a change in the amplitude value of the pair of vibrator subassemblies in response to a change in the driving current in an output of the detector, in addition to the constituent elements of the known vibration-type viscometers as described above. Since the continuous change in the magnitude of the driving current with respect to the driving unit appears in the continuous change in the vibration-applying force to the pair of vibrator subassemblies, if the change in the amplitude of vibrator due to the change in the vibration-applying force is continuously detected, it is possible to measure the rate of change with time in the motion of a fluid. In this case, in contrast with the rheometer using a conventional rotary viscometer for generating a concentric circular flow in the fluid, slight vibratIons are merely generated by the pair of vibrator subassemblies according to the present invention, and therefore the measuring pattern resulting from the control of the applying the vibration-applying force and the magnitude may have a considerable freedom. The control of the manner of applying the vibration-applying force and the magnitude may have a considerable freedom. The control of the driving current in typical examples of the measuring pattern is as follows:

Pattern 1: From time t0 to t1, steplessly and continuously increased, and then from t1 to t2, steplessly and continuously decreased.

Pattern 2: Similar to the pattern 1, continuously increased till the time t1, and held constant after the time t1.

Pattern 3: Similarly to the pattern 1, continuously increased till the time t1, and thereafter held constant till the next time t2, and then cut off to 0.

Pattern 4: Similar to the pattern 1, continuously increased till the time t1, and conversely steplessly and continuously lowered from the time t1 to the next time t2. These up and down cycles are repeated.

These measuring patterns can be obtained easily by program-controlling the driving current.

According to the present invention, the driving current applied to the driving unit may, for example, be steplessly an continuously changed and the change in the amplitude value due to the change in the vibrationapplying force in the pair of vibrator-subassemblies is continuously detected whereby the rheology of the fluid can be measured. Therefore, the measurement can be simply conducted without giving rise to a problem in handling encountered in the use of a conventional rotary viscometer.

BRIEF DESCRIPTION OF THE DRAWINGS

FIG. 4 is of the case where a sample is mayonnaise, FIG. 5 is of the case where a sample is cold cream, and FIG. 6 is of the case where a sample is milky liquid.

DETAILED DESCRIPTION OF THE PREFERRED EMBODIMENTS

Figure 3:
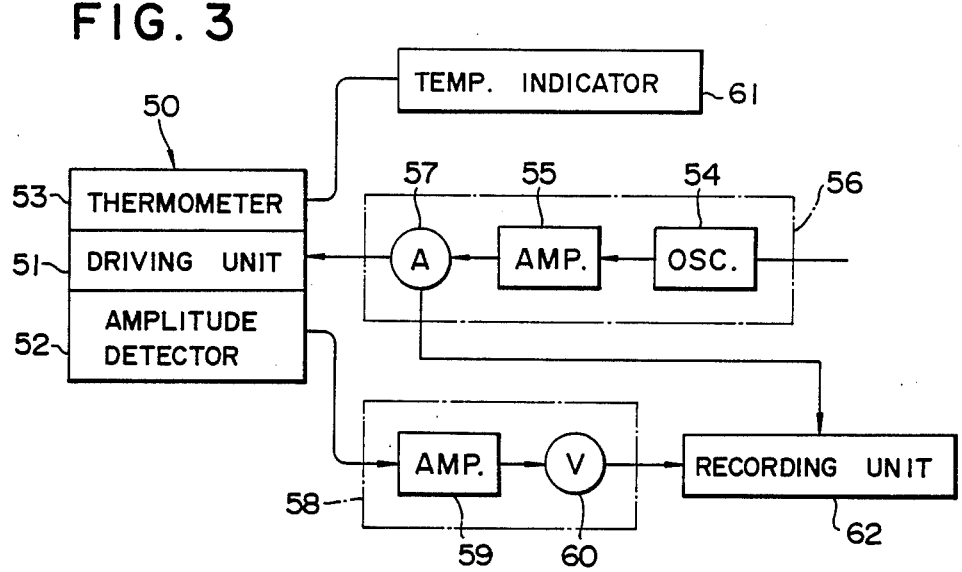
FIG. 3 is a block diagram for explaining an amplitude rheometer apparatus according to the present invention.

First, referring to FIG. 3, a vibration-type rheometer apparatus according to the present invention includes a vibration-type viscometer generally indicated at 50. This vibration-type viscometer comprises an electromagnetic driving unit 51, an amplitude detector 52 and a thermometer 53, which will be described in detail later. The electromagnetic driving unit 51 has a permanent magnet 13 (FIG. 1) and an electromagnetic coil 12 (FIG. 1) cooperating therewith, the electromagnetic coil 12 receiving a driving current, whose magnitude steplessly and continuously changes, from a control unit 56 including an oscillator 54 and a variable amplifier 55. This control unit 56 is provided with an ammeter 57 for measuring the magnitude of the driving current to be supplied to the electromagnetic driving unit 51. On the other hand, the amplitude detector 52 comprises, for example, a non-contact system eddy current loss detection type displacement detector 14 (FIG. 1), and an output signal of this detector 14 is sent to an amplitude display unit 58. This amplitude display unit 58 includes an amplifier 59 connected to an output side of the detector 14 and a voltmeter 60 for measuring an output of the amplifier 59 as a voltage value. The thermometer 53 has a temperature probe 21 (FIG. 1), an output signal of which is supplied to a temperature indicator 61 A value measured by the ammeter 57 and a value measured by the voltmeter 60 are sent to a recording or processing unit 62 such as an X-Y recorder, and the recording unit 62 plots a detection voltage representative of a change in an amplitude value from the amplitude detector 52 corresponding to a driving current having a magnitude which continuously and steplessly changes sent to the electromagnetic driving unit 51.

Figure 1:
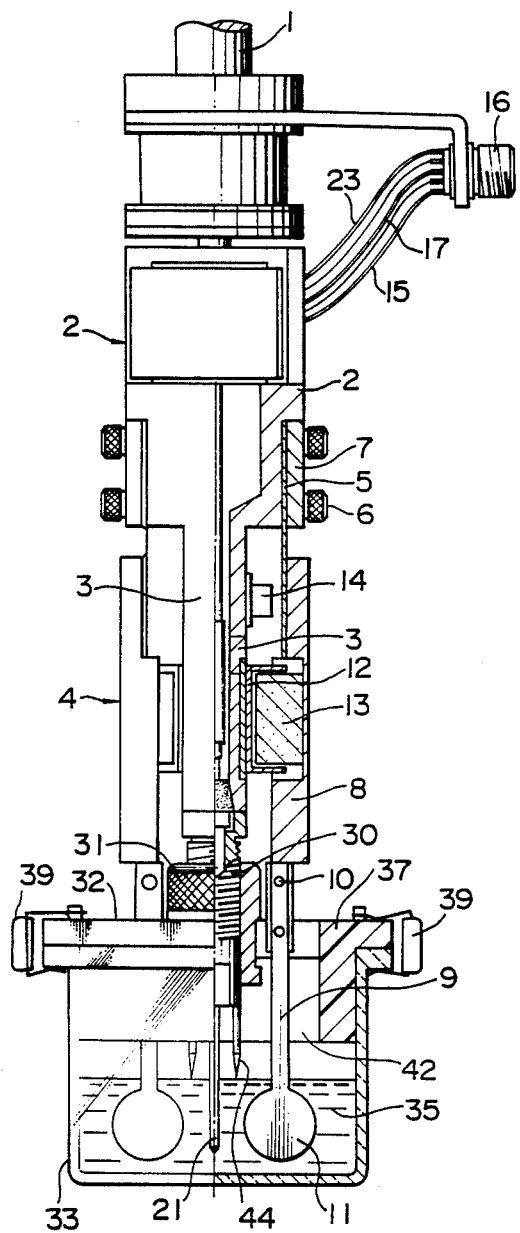
FIG. 1 is a partial cut-away side elevational view of a vibration-type viscometer used in the present invention.

The vibration-type viscometer per se used in the present invention is disclosed in U.S. Pat. Nos. 4,602,505 and 4,729,237. Referring to FIG. 1, the vibration-type viscometer is provided with a hollow support block 2 formed of a rigid material firmly secured to a frame shaft 1 extending from a base (not shown), the support block 2 having a downwardly extending support column 3. A pair of vibrator subassemblies 4 constituting tuning fork-like vibrators are secured to the lower end of the support block Z, and these vibrator subassemblies 4 downwardly extend from the support block 2 and occupy sides opposite each other of the support column 3. The vibrator subassemblies 4 each include a leaf spring 5 with one end secured to the support block 2 by means of a screw 6 through a stop 7, a long intermediate plate 8 firmly mounted on the other end of the leaf spring 5, and a sensor plate 9 secured to the end of the intermediate plate 8 by means of a screw 10. The leaf spring 5 is preferably made of constant elastic spring steel, and the intermediate plate 8 is preferably made of a relatively light material having a rigidity, for example, such as aluminum. The sensor plate 9 is preferably made of stainless steel which is as thin as 0.2 mm or so, is flat and has a chemical resistance, the sensor plate having a free end formed into a disk 11 having a diameter of 20 mm or so, for example.

One vibrator subassembly 4 is arranged symmetrically with the other vibrator assembly, and a permanent magnet 13 which cooperators with a pair of electromagnetic coils 12 mounted on the support column 3 is provided on the intermediate plate 8. The combination of the electromagnetic coils 12 and the permanent magnet 13 functions as a driving device 51 for vibrating the corresponding vibrator subassemblies 4, the driving device 51 being supplied with a driving current having a magnitude which steplessly and continuously changes from the control unit 56 (FIG. 3) as described above to thereby vibrate the pair of vibrator assemblies 4 by a vibration-applying force having a magnitude which steplessly and continuously changes in phases opposite to each other, that is, a phase difference of 180 degrees under the same frequency. According to a desireable example, the driving frequency is 30 Hz, and the driving current linearly changes from 0 to 1000 mA. The pair of sensor plates 9 are distributed within the same imaginary vertical plane, and as a result, a torsional reaction in the support block 2 generated in the case where the sensor plates, are distributed in the different imaginary vertical planes can be avoided. While the relative arrangement of the electromagnetic coils 12 and the permanent magnet 13 may be reversed, the provision of the electromagnetic coils 12 on the side of the support column 3 as in the example shown in the drawing is suitable in that a lead wire 15 of the coil 12 can be guided to a terminal metal 16 (upward) passing through the support column 3.

The support column 3 between the support block 2 and the electromagnetic coil 12 is provided with a displacement detector 14 opposed to the leaf spring 5 of the vibrator subassembly 4, the displacement detector 14 converting the amplitude of one vibrator subassembly 4 into an electric signal. In this case, a further displacement detector may be provided for the other vibrator subassembly, but since both the vibrator subassemblies 4 exhibit substantially the same amplitude, one will suffice. When the pair of sensor plates 9 are placed into a sample as will be described later, the amplitude of the vibrator subassemblies 14 is affected by the change in the viscous resistance, and therefore the displacement detector 14 electrically detects the amplitude, and the viscosity of the sample is arithmetically calculated from that detected value in a well known manner. The displacement detector 14 can be, for example, of a well known non-contact system eddy current loss detector but in the case where this well known displacement detector is used, the leaf spring 5 opposed thereto is formed of a magnetic spring steel. A well known optical displacement sensor can be also used in place of an eddy current loss detection type displacement sensor. A lead wire 17 of the displacement detector 14 is also guided to a common terminal element 16 passing through the support column 3.

Figure 2:
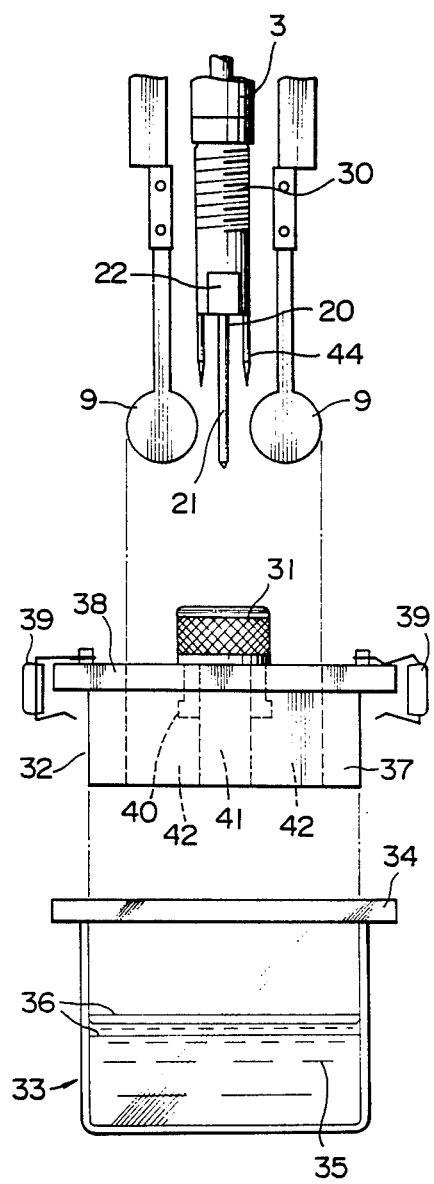
FIG. 2 is a side view showing essential parts shown in FIG. 1 in an exploded form.

Turning to FIG. 2, a thermometer generally indicated at 20 is mounted on the lower end of the support column 3, and a sheathed probe 21 of the thermometer 20 extends downward. This temperature probe 21 occupies an intermediate position between the pair of sensor plates 9 and is distributed in the same imaginary vertical plane, the probe 21 having its lower end distributed in substantially the same imaginary horizontal plane as the pair of the sensor plates 9. Since the temperature probe 21 is aligned in the same imaginary vertical plane as the pair of sensor plates 9, an occurrence of sample turbulence due to the presence of the temperature probe 12 between these sensor plates is prevented. The thermometer 20 can be of a well known type, for example, in which a platinum temperature measuring resistance is provided within a sheath, which well known thermometer has a circuit unit 22 including an amplifier at the base end of the sheath. A lead wire 23 of the circuit unit 22 reaches a common terminal element 16 passing through the support column 3.

An external thread 30 is formed at the lower end of the support column 3, and a carrier device 32 having an adjusting nut member 31 threadedly engaged with the external thread 30 is mounted on the support column 3. The carrier device 32 detachably carries a sample container 33, and functions as a lid for closing an open end of the sample container 33. The sample container 33 is conveniently made from a transparent glass like a beaker. This container has a flange 34 around the open edge thereof, and has an index comprising two parallel lines 36 representative of an allowable amount of a sample 35 to be placed therein. The carrier device 32 includes a lid member 37 formed of a synthetic resin excellent, for example, in heat insulating property having a plane size just fitted into the sample container 33, the lid member 37 having a flange 38. The lid member 37 is provided with a pair of well known clamp elements 39, and when these clamp elements 39 are brought into engagement with the flange 34 of the sample container 33, the sample container 33 can be mounted on the carrier device 32. The adjusting nut member 31 threadedly engaged with the external thread 30 of the support column 3 has a stopper 40 at the lower part thereof, and the axial movement is restricted by the stopper 40. The lid member 37 is formed with a hole 41 through which the lower end of the support column 3 may pass and a pair of head-diffusion preventive narrow slits 42 through which the pair of sensor plates 9 may pass.

Normally, the carrier device 32 is mounted on the lower end of the support column 3, and the sample container 33 is detachably mounted on the carrier device 32. Two pins 44 are downwardly secured to the lower end of the support column 3, the pins 44 being located on opposite sides of the temperature probe 21, occupying a position between the probe and the sensor plate 9 and being aligned in the imaginary vertical plane in which the sensor plates 9 and the temperature probe 2 ar distributed. The pens 44 each have an end tip which functions as an indicator representative of a desirable surface level of the sample 35 within the container 33. More specifically, if there is non-coincidence between the end tips of the pin 44 and the surface level of the sample 35, the adjusting nut member 31 of the carrier device 32 is rotated to axially move the sample container 33 along with the carrier device 32 toward the support column 3, until the end tips are coincident with the sample surface. As a result, even if samples in different amounts within an allowable range between the two index lines 36 are provided in the sample container 33, the sensor plates 9 and the temperature probe 21 can be always inserted by a predetermined length into the sample without difficulty and it is not necessary that the sample be provided in the sample container 33 in a strictly determined amount.

Figure 4:
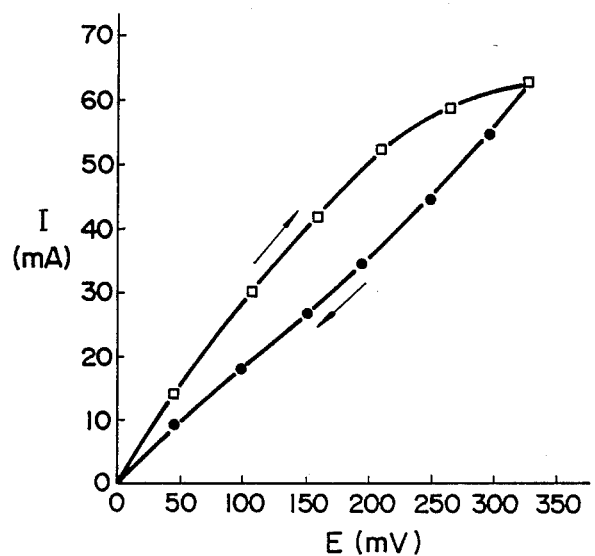
FIGS. 4, 5 and 6 are respectively explanatory views showing the flow characteristics of a sample measured by the vibration-type rheometer apparatus according to the present invention.
Figure 5:
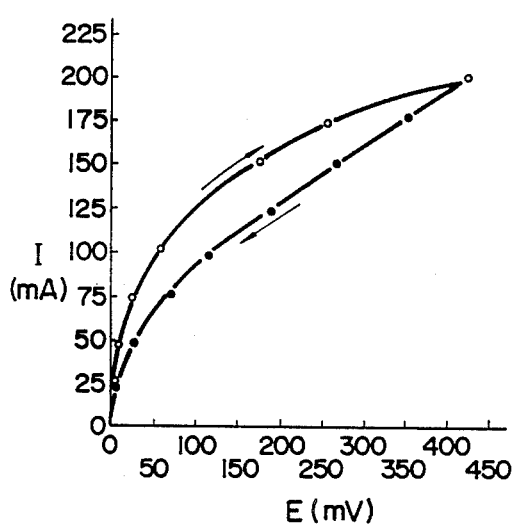
Figure 6:
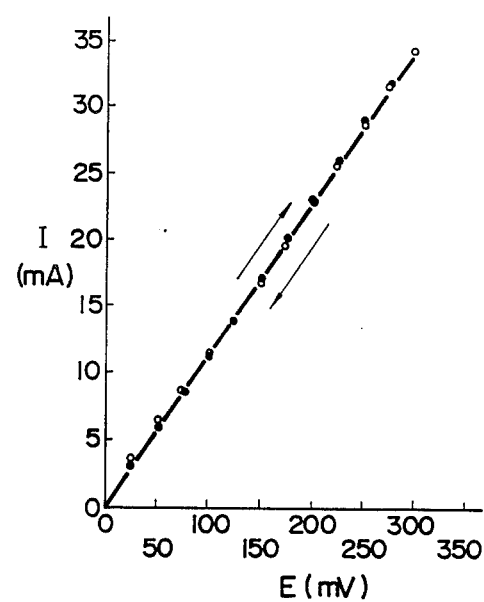

FIGS. 4, 5 and 6 are respectively graphs showing the results obtained by measuring the flow characteristics of three kinds of samples during a measuring cycle using a vibration-type rheometer manufactured in accordance with the preferred example of the present invention. In these graphs, the axis of ordinate indicates the magnitude of a driving current signal I corresponding to a vibration-applying force applied to the pair of vibrator subassemblies 4 while the axis of abscissa indicates the magnitude of the detected voltage signal E corresponding to the amplitude of the pair of vibrator subassemblies 4. In this case, FIG. 4 of the case where the sample is mayonnaise, FIG. 5 is of the case where the sample is cold cream, and FIG. 6 is of the case where the sample is milky liquid. According to FIGS. 4 and 5, a curve obtained by gradually increasing the vibration-applying force and a curve, obtained by gradually decreasing the vibration-applying force depict a hysteresis loop, from which can be learned that these samples exhibit a thixotropyic non-Newtonian viscosity. According to FIG. 6, it can be seen that the change in the amplitude with respect to the change in the vibration-applying force is linear, and this sample is a material exhibiting a Newtonian viscosity.

Figure 7A:
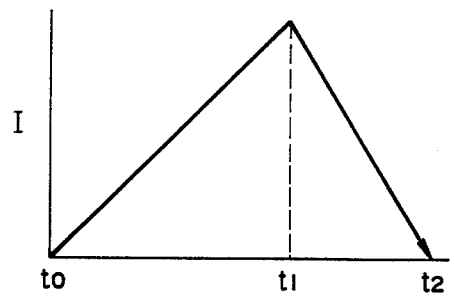
FIGS. 7a–7d are explanatory graphs representative of various measuring patterns.

FIGS. 7a-7d are graphs showing the state of driving current in various measuring patterns, and in each graph, the axis of ordinate indicates the current value I and the axis of abscissa indicates the time T. The states of the measuring patterns represented by these graphs are as follows:

FIG. 7a—pattern 1: From time t0 to t1, driving current increased steplessly and continuously, and then from t1 to t2, decreased steplessly and continuously.

Figure 7B:
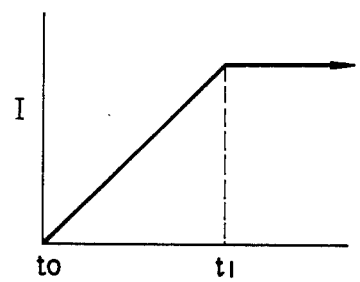

FIG. 7b—pattern 2: Similar to the pattern 1 in that the driving current is increased continuously till time t1, but then held constant after the time t1.

Figure 7C:
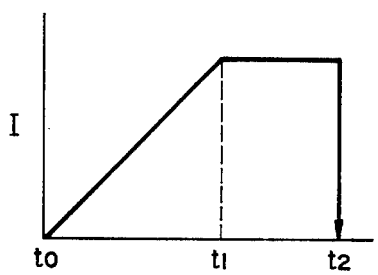

FIG. 7c—pattern 3: Similar to the pattern 12 in that the driving current is increased continuously till time t1, but thereafter held constant till time t2, and then abruptly cut off to 0.

Figure 7D:
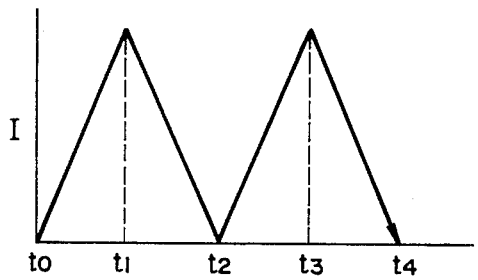

FIG. 7d—pattern 4: The driving current is increased steplessly and continuously from time to time t1, and then lowered steplessly and continuously from time t1 to time t2.

These up and down cycles are repeated.

The aforementioned measuring patterns merely comprise exemplary embodiments, and according to the present invention various modifications can be made and the invention is not limited to these measuring patterns.

What is claimed is:

1. A vibration-type rheometer apparatus for measuring the behavior of a fluid sample with respect to an external force which changes with time, the apparatus comprising:

a support block firmly secured to a base frame, said support block having a support column at the lower part thereof;

tuning fork vibrator means including a pair of vibrator subassemblies secured to said secured block, extending downwardly from said support block and being arranged on opposite sides of said support column, said vibrator subassemblies each having at a free end thereof a thin and flat sensor plate to be placed into a fluid sample to be measured, both said sensor plates being distributed in the same imaginary vertical plane;

driving means for vibrationally driving said pair of vibrator subassemblies in opposite phase relation to each other and at the same driving frequency;

detecting means for detecting the amplitude of vibration of at least one of said vibrator subassemblies which changes by the viscous resistance received by said sensor plates placed in the fluid sample and for outputting an electric signal representative of the amplitude of vibration;

control means for supplying a driving current having a magnitude which changes with respect to time to said driving means to thereby change a vibration-applying force applied to said pair of vibrator subassemblies; and recording means for plotting, with respect to the change in magnitude of said driving current, the electric signal output from said detecting means which changes in response to changes in the driving current.

2. The vibration-type rheometer apparatus according to claim 1; wherein said control means includes an oscillator for producing an output signal having a fixed frequency, a variable amplifier for amplifying the output signal to produce a driving current having a magnitude which changes with time, and an ammeter for measuring the magnitude of the driving current.

3. The vibration-type rheometer apparatus according to claim 1; wherein said control means includes means for producing a driving current having a magnitude which changes with time according to one of a plurality of predetermined patterns.

4. The vibration-type rheometer apparatus according to claim 3; wherein said control means includes a pattern for controlling the magnitude of said driving current such that the magnitude is steplessly and continuously increased from a time t0 to a time t1, and held constant after the time t1.

5. The vibration-type rheometer apparatus according to claim 3; wherein said control means includes a pattern for controlling the magnitude of said driving current such that the magnitude is steplessly and continuously increased from a time t0 to a time t1, and held constant from the time t1 to a time t2, and then cut off to 0 at the time t2.

6. The vibration-type rheometer apparatus according to claim 3; wherein said control means includes a pattern for controlling the magnitude of said driving current such that the magnitude is steplessly and continuously increased from a time t0 to a time t1, and steplessly and continuously lowered from the time t1 to a time t2.

7. An apparatus for measuring rheological properties of a fluid sample, comprising: a pair of vibrating means operative when driven to undergo vibrational movement in opposite phase relation to one another, each vibrating means having at a free end thereof a sensor plate which is immersed in a fluid sample during use of the apparatus; driving means responsive to an electrical driving signal for effecting vibrational movement of the pair of vibrating means accompanied by vibrational movement of the sensor plates within the fluid sample; control means for producing an electrical driving signal having a magnitude which varies with time according to a predetermined pattern during a measuring cycle and for applying the electrical driving signal to the driving means to accordingly vary the vibrational movement of the pair of vibrating means; detecting means for detecting the amplitude of vibration of at least one of the vibrating means and producing a corresponding electrical detection signal; and processing means for processing the electrical driving signal in conjunction with the electrical detection signal to derive therefrom data representative of the rheological property of the fluid sample.

8. An apparatus according to claim 7; wherein the control means includes means for producing an electrical driving signal having a magnitude which varies continuously with time during a major portion of the measuring cycle.

9. An apparatus according to claim 7; wherein the control means includes means for producing an electrical driving signal having a magnitude which continuously increases from a time t0 to a time t1 during the measuring cycle.

10. An apparatus according to claim 9; wherein the means for producing an electrical driving signal produces an electrical driving signal having a magnitude which continuously decreases from the time t1 to a time t2 during the measuring cycle.

11. An apparatus according to claim 10; wherein the means for producing an electrical driving signal produces an electrical driving signal having a magnitude which continuously increases from the time t2 to a time t3 and which continuously decreases from the time t3 to a time t4 during the measuring cycle.

12. An apparatus according to claim 9; wherein the means for producing an electrical driving signal produces an electrical driving signal having a magnitude which is constant from the time t1 to a time t2 during the measuring cycle.

13. An apparatus according to claim 12; wherein the means for producing an electrical driving signal produces an electrical driving signal having a magnitude which is abruptly reduced to 0 at the time t2.

14. An apparatus according to claim 7; wherein the processing means includes means for coincidently processing the electrical driving and detection signals.

15. An apparatus according to claim 7; wherein the processing means includes means for plotting the electrical driving signal as a function of the electrical detection signal.

16. An apparatus according to claim 7; wherein the control means includes means for producing a driving current signal; and the detecting means includes means for producing a detection voltage signal.

17. An apparatus according to claim 16; wherein the processing means includes means for plotting the driving current signal as a function of the detection voltage signal.

* * * * *